(12) United States Patent
Wang et al.

(10) Patent No.: US 7,886,413 B2
(45) Date of Patent: Feb. 15, 2011

(54) METHOD FOR IMPROVED STABILIZATION OF A TAMPON

(75) Inventors: Fancheng Wang, Blue Ash, OH (US); Rebecca White Patterson, Cincinnati, OH (US); Thomas Ward Osborn, III, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 487 days.

(21) Appl. No.: 11/968,834

(22) Filed: Jan. 3, 2008

(65) Prior Publication Data
US 2009/0177175 A1    Jul. 9, 2009

(51) Int. Cl.
*A61F 13/20* (2006.01)
(52) U.S. Cl. .......................................... 28/118
(58) Field of Classification Search ............... 28/118, 28/119, 120, 122; 8/115.51, 116.1; 604/385.17, 604/904, 385.18
See application file for complete search history.

(56) References Cited

U.S. PATENT DOCUMENTS

| | | | |
|---|---|---|---|
| 2,440,141 A * | 4/1948 | Donovan ................ | 604/363 |
| 3,995,636 A | 12/1976 | Murray et al. | |
| 4,179,416 A | 12/1979 | Smith | |
| 4,326,527 A | 4/1982 | Wollangk et al. | |
| 4,327,174 A | 4/1982 | Von Meer | |
| 5,220,346 A | 6/1993 | Carreira et al. | |
| 5,387,207 A | 2/1995 | Dyer et al. | |
| 5,849,805 A | 12/1998 | Dyer | |
| 6,261,679 B1 | 7/2001 | Chen et al. | |
| 6,353,146 B1 | 3/2002 | Williams | |
| 6,532,683 B1 | 3/2003 | Bryant | |
| 6,603,054 B2 | 8/2003 | Chen et al. | |
| 6,702,797 B2 | 3/2004 | Williams | |
| 6,740,070 B2 | 5/2004 | Agyapong et al. | |
| 6,837,882 B2 | 1/2005 | Agyapong et al. | |
| 7,047,608 B2 | 5/2006 | Sageser et al. | |
| 7,089,685 B2 | 8/2006 | Torgovnikov et al. | |
| 7,120,977 B2 | 10/2006 | Bittner et al. | |
| 7,124,483 B2 * | 10/2006 | Prosise et al. .......... | 28/118 |
| 7,472,463 B2 * | 1/2009 | Gilbert et al. .......... | 28/118 |
| 2001/0024716 A1 | 9/2001 | Chen et al. | |
| 2002/0133133 A1 | 9/2002 | Agyapong et al. | |
| 2003/0172504 A1 * | 9/2003 | Sageser et al. ......... | 28/118 |

(Continued)

FOREIGN PATENT DOCUMENTS

AU    414602    6/1971

(Continued)

OTHER PUBLICATIONS

PCT International Search Report dated Apr. 15, 2009.

(Continued)

*Primary Examiner*—Amy B Vanatta
(74) *Attorney, Agent, or Firm*—Amanda T. Barry (57) ABSTRACT

A method is provided for stabilizing a tampon. The method includes providing a pledget having a moisture content and including one or more metallic cation salts, compressing the pledget to produce a tampon, and applying microwave radiation to the tampon for a time sufficient to stabilize the tampon. The time to stabilize a tampon can be reduced by at least about 20% compared to the time to stabilize a tampon lacking one or more metallic cation salts.

20 Claims, 7 Drawing Sheets

U.S. PATENT DOCUMENTS

| | | |
|---|---|---|
| 2003/0233742 A1 | 12/2003 | Jones et al. |
| 2006/0235361 A1 | 10/2006 | Agyapong et al. |
| 2007/0151147 A1 | 7/2007 | Learey et al. |
| 2007/0207273 A1 | 9/2007 | English et al. |
| 2008/0119811 A1* | 5/2008 | Gilbert et al. .......... 604/385.17 |

FOREIGN PATENT DOCUMENTS

| | | | |
|---|---|---|---|
| EP | 0 138 427 | B1 | 3/1990 |
| EP | 1 534 206 | B1 | 8/2007 |
| JP | 2006 117478 | A | 5/2006 |
| JP | 2006 329462 | A | 12/2006 |
| JP | 2006 6329462 | A | 12/2006 |
| JP | 2007 098358 | A | 4/2007 |

OTHER PUBLICATIONS

Forest Products Project Fact Sheet "Application of a Device for Uniform Web Drying and Preheating Using Microwave Energy", Office of Industrial Technologies, Energy Efficiency and Renewable Energy, U.S. Department of Energy, Oct. 2000.

* cited by examiner

METHOD FOR IMPROVED STABILIZATION OF A TAMPON

FIELD OF THE INVENTION

The invention relates to methods for improved stabilization of tampons, and more particularly to methods for improved stabilization of tampons using microwave drying.

BACKGROUND OF THE INVENTION

Tampons for feminine hygiene are typically made from fibers that have been compressed, in some manner, into a substantially cylindrical form. These fibers can have a tendency to re-expand to their original dimensions after a compression step, unless the fibers are stabilized in the compressed state. Generally, tampons are stabilized by either conductive heating or microwave heating.

Conductive heating methods typically do not uniformly stabilize the tampon and can result in the alteration of absorbent qualities in the outer layer of the tampon, as the outside of the tampon can dry more quickly than the inside. Conductive heating methods can also be time and energy intensive, as the air within the tampon must be heated, to dry the fibers via conduction from outside the tampon to the inside. Furthermore, high temperatures that could decrease cycle times cannot be utilized in conductive heating methods. The high temperatures may be above the melting point of portions of the tampon, such as the overwrap, which can result in a melted product.

While microwave heating can be a faster method of stabilizing tampons than conductive heating, only a small fraction of the outputted energy used in microwave heating is actually utilized to stabilize the tampon. As a result of this inefficiency, the energy costs of this method are relatively high.

As such, it would be desirable to provide a method for stabilizing tampons, by drying them that can reduce energy utilization. It would also be desirable to provide a method of drying tampons that can provide increased speed of tampon production.

SUMMARY OF THE INVENTION

A method for stabilizing a tampon is provided. The method comprises the steps of providing a pledget having a moisture content and comprising one or more metallic cation salts. The pledget is compressed to produce a tampon having a moisture content and comprising one or more metallic cation salts. Microwave radiation is then applied to the tampon for a time sufficient to stabilize the tampon. Using this method it is believed the stabilization time is reduced when compared to the stabilization time for a tampon having a moisture content, but lacking one or more metallic cation salts.

A method for stabilizing a tampon is provided. The method comprises the steps of providing a pledget comprising one or more metallic cation salts. The pledget is compressed to produce a tampon comprising one or more metallic cation salts. The tampon is then provided with a moisture content. Microwave radiation is then applied to the tampon for a time sufficient to stabilize the tampon. Using this method it is believed the stabilization time is reduced when compared to the stabilization time for a tampon having a moisture content, but lacking one or more metallic cation salts.

A method for stabilizing a tampon is provided. The method comprises the steps of providing a pledget. The pledget is compressed to produce a tampon. The tampon is then provided with a moisture content and one or more metallic cation salts. Microwave radiation is then applied to the tampon for a time sufficient to stabilize the tampon. Using this method it is believed the stabilization time is reduced when compared to the stabilization time for a tampon having a moisture content, but lacking one or more metallic cation salts.

DETAILED DESCRIPTION OF THE INVENTION

The present invention provides methods for stabilizing tampons using microwave drying. Surprisingly, the addition of metallic cation salts to a tampon or pledget, for example by adding metallic cation salts to liquids, such as water to wet or moisten the absorbent material of a tampon or pledget, or metallic cation salts added during tampon or pledget processing, can substantially reduce the time usually required to dry the absorbent material when the absorbent material is heated by microwave radiation. Such increased drying speed can increase the output of tampons produced, which can, for example, reduce processing and energy costs.

As used herein, the term "absorbent article" refers to any type of article used for the absorption of bodily fluids such as urine, blood, or menses. Absorbent articles include an absorbent material and may take many forms, such as tampons, sanitary napkins, interlabial products, incontinence pads, diapers, surgical wound dressings, sponges, nasal packings, other absorbent articles intended for feminine, medical, dental, surgical or nasal use.

As used herein, the term "tampon" refers to any type of absorbent article that is inserted into the vaginal canal for the absorption of fluid therefrom. Typically, tampons are constructed from an absorbent material, which may be in the form of a pledget that has been compressed into a vaginally insertable shape.

As used herein, the term "pledget" refers to a construction of absorbent material prior to the compression of such construction into a tampon.

The term "absorbent material" as used herein can be constructed from a wide variety of materials commonly used in absorbent articles. Such materials include, but are not limited to synthetic fibers, natural fibers, or combinations thereof. The natural fibers may include, but are not limited to, cotton, wood pulp, flax, hemp, and rayon, such as GALAXY Rayon (a tri-lobed rayon structure) available as 6140 Rayon; or SARILLE L rayon (a round fiber rayon), both available from Kelheim Fibers of Kelheim, Germany, cotton, wood pulp, flax, and hemp. The synthetic fibers can include, but are not limited to, fibers such as polyester, polyolefin, nylon, polypropylene, polyethylene, polyacrylic, vinyl polyacetate, polyacrylate, cellulose acetate, or bicomponent fibers, such as bicomponent polyethylene and polypropylene fibers. Additional absorbent material include materials such as, peat moss, absorbent foams (such as those disclosed in U.S. Pat. No. 3,994,298), capillary channel fibers (such as those disclosed in U.S. Pat. No. 5,356,405), high capacity fibers (such as those disclosed in U.S. Pat. No. 4,044,766), superabsorbent polymers or absorbent gelling materials (such as those disclosed in U.S. Pat. No. 5,830,543), may be incorporated into the tampon.

As used herein, "vaginally insertable shape" refers to the geometrical form of a tampon after compression. To form a tampon, a pledget can be compressed into a generally cylindrical configuration. A tampon can be radially compressed, wherein radial compression provides for deformation generally orthogonal to the longitudinal axis. A tampon can also be longitudinally compressed, wherein longitudinal compression provides for deformation generally parallel to the longitudinal axis. An example of a typical tampon size is a tampon that is about 10-16 mm wide and about 30-55 mm long depending on absorbency. While the tampon can be compressed into a substantially cylindrical configuration, other shapes are possible. These may include shapes having a cross section that can be described as rectangular, triangular, trapezoidal, semi-circular, hourglass, or other suitable shapes.

The term "attached" as used herein, encompasses configurations such as: a first element directly attached to a second element; configurations in which a first element is indirectly attached to a second element by attaching the first element to one or more intermediate members, which in turn are attached to the second element; and configurations in which a first element is integral with a second element, for example a first element that is essentially part of the second element.

As used herein, "compression" refers to the method of pressing, squeezing, compacting or otherwise manipulating the size, shape, or volume of a pledget to produce a tampon having a vaginally insertable shape. The term "compressed" refers to the state of an absorbent material or absorbent materials, which may be in the form of a pledget, subsequent to compression. Conversely, the term "uncompressed" refers to the state of an absorbent material or absorbent materials, which may be in the form of a pledget, prior to compression. The term "compressible" is the ability of a material to undergo compression.

As used herein, "mold" refers to a structure for shaping a pledget during compression or for retaining the shape of a compressed tampon subsequent to compression, such as prior to or during stabilization of the tampon.

The term "stabilized," as used herein, refers to a tampon in a self-sustaining state wherein it has overcome the natural tendency to re-expand to the pledget's pre-compression size, shape and volume, absent the application of external force. As used herein "stabilization time" refers to the length of time beginning with the application of microwave radiation and ending when the tampon is in a substantially self-sustaining state. The term "self-sustaining" is a measure of the degree or sufficiency to which a tampon retains its compressed form after stabilization, such that in the absence of external forces the resulting tampon substantially retains its vaginally insertable shape and size. For example, in certain embodiments, a stable tampon's size will not increase more than 20% after the tampon has been stabilized, but prior to the tampon's exposure to liquids, such as menses. In certain other embodiments, a stable tampon's size will not increase more than 15% after the tampon has been stabilized, but prior to the tampon's exposure to liquids, such as menses. In still further embodiments, a stable tampon's size will not increase more than 10% after the tampon has been stabilized, but prior to the tampon's exposure to liquids, such as menses. For tampons, it is found that control of the level of moisture (moisture content) within the tampon is a factor for helping the tampon to retain its shape in the absence of the external compression forces. In certain embodiments, the moisture content of a tampon is reduced after stabilization as compared to the moisture content of the tampon prior to stabilization. Therefore, to stabilize a tampon the tampon's moisture content is reduced, that is heat is usually applied to a tampon in order to dry it. This self-sustaining form need not persist during actual use of the tampon. That is, once the tampon is inserted into the vagina or other body cavity and begins to acquire fluid the tampon may lose its self-sustaining form due to expansion.

The method for improved stabilization using microwave drying can be applied to any suitable absorbent article. In certain embodiments, the method for improved stabilization using microwave drying can include the steps of, for example, providing a pledget having a moisture content and one or more metallic cation salts. The pledget is then compressed to produce a tampon. Microwave radiation can then be applied to the tampon to reduce the tampon's moisture content (drying), in order to stabilize the tampon. In certain embodiments, the method for improved stabilization using microwave drying can include the steps of, for example, providing a pledget having one or more metallic cation salts. The pledget is then compressed to produce a tampon. During or following compression the tampon is provided with a moisture content. Microwave radiation can then be applied to the tampon to reduce the tampon's moisture content (drying), in order to stabilize the tampon. In still further embodiments, the method for improved stabilization using microwave drying can include the steps of, for example, providing a pledget. The pledget is then compressed to produce a tampon. During or following compression the tampon is provided with a moisture content and one or more metallic cation salts. Microwave radiation can then be applied to the tampon to reduce the tampon's moisture content (drying), in order to stabilize the tampon. The above mentioned steps can be performed in any order suitable for stabilizing a tampon according to the present invention.

In certain embodiments, a pledget can be compressed into a mold to form a tampon. In addition, or alternatively, a pledget can be partially compressed with the final compression being completed when pushing the pledget into a mold. For example, the method for improved stabilization by using microwave drying can be used in conjunction with methods disclosed in, e.g., U.S. Pat. Nos. 6,554,814; 6,682,513; 6,740,070; 6,837,882 and 7,047,608.

Providing a moisture content to a tampon or pledget can be accomplished in any suitable manner, such as, by placing the tampon or pledget in a humidification chamber maintained at a suitable temperature and humidity until the tampon or pledget is in moisture equilibrium with the chamber. A pledget or tampon can have any suitable moisture content. Moisture content can be measured in any suitable manner, for example by determining the weight difference between a tampon prior to exposure of microwave radiation and after exposure to microwave radiation. Moisture content may also be determined by the TAPPI method T 412. For example, in certain embodiments, the pledget or tampon can have pre-stabilization moisture content greater than about 20%, for example greater than about 30%, greater than about 40%, greater than about 50%, greater than about 60%, greater than about 70%, greater than about 80%, greater than about 90%, or more moisture by weight of the pledget or tampon prior to the step of applying microwave radiation to the tampon formed from the pledget. In certain embodiments, after the application of microwave radiation for stabilization a tampon can have a final moisture content, in the range of from less than about 20% to about 0% moisture by weight. In certain embodiments, after the application of microwave radiation for stabilization a tampon can have a final moisture content, in the range of from less than about 10% to about 5% moisture by weight.

Microwave radiation can be applied at any suitable power level. Suitable power levels include, for example, about 1 kW, about 1.5 kW, about 2 kW, about 2.5 kW, about 3 kW, about 3.5 kW, about 4 kW, about 4.5 kW, about 5 kW, about 5.5 kW, about 6 kW, about 6.5 kW, about 7 kW, about 7.5 kW, about 8 kW, about 8.5 kW, about 9 kW, or more. Microwave radiation can be supplied in a suitable manner, such as by using a machine capable of generating microwaves.

In certain embodiments, the microwave drying time for stabilizing a tampon having one or more metallic cation salts can be reduced compared to the microwave drying time for stabilizing a tampon lacking one or more metallic cation salts. For example, the microwave drying time for stabilizing a tampon can be reduced by any suitable amount, such as at least about 20%, at least about 25%, at least about 30%, at least about 35%, at least about 40%, at least about 45%, at least about 50%, or more, as compared to the microwave drying time for stabilizing a tampon lacking one or more metallic cation salts. Further, the microwave drying time for stabilizing a tampon comprising one or more metallic cation salts can be at least about 1.2 times faster, about 1.5 times faster, about 2 times faster, about 2.5 times faster, about 3 times faster, about 3.5 times faster, about 4 times faster, about 4.5 times faster, about 5 times faster, or more, as compared to the microwave drying time for stabilizing a tampon lacking one or more metallic cation salts.

Any suitable metallic cation salt can be added. In certain embodiments, the metallic cation salt may be an inorganic metallic cation salt, for example, calcium salts, such as calcium chloride, ferric salts, such as ferric chloride, magnesium salts, such as magnesium chloride, sodium salts, such as sodium chloride, strontium salts, barium salts, aluminum salts, copper salts, zinc salts, potassium salts, or any other suitable metallic cation salt, or combinations thereof. In certain embodiments, the metallic cation salt may be an organic metallic cation salt, for example, calcium salts such as calcium lactate and calcium citrate malate.

A metallic cation salt can be added in any suitable concentration such as from about 2 mM, about 2.5 mM, about 3 mM, about 3.5 mM, about 4 mM, about 4.5 mM, about 5 mM, about 10 mM, about 15 mM, about 30 mM, about 50 mM, about 100 mM, about 150 mM, about 200 mM or more. In addition, the metallic cation salt can be added in any suitable form, such as in solution with any suitable solvent, for example water, or in solid form, for example an emulsion in the fiber melt.

The metallic cation salt can be added at any suitable time and in any suitable manner. For example, in certain embodiments, metallic cation salt solution can be added by the application of moisture directly to the pledget or tampon, such as, by spraying, by immersion, or during fiber formation. In addition, or alternatively, metallic cation salt can be added in any suitable form to a tampon or pledget.

A pledget can be any suitable shape, size, volume, material, or construction prior to compression. For example, the pledget can include a rolled, tubular, or flat construction of an absorbent material that can be a circle, an oval, a semi-circle, a triangle, a chevron shape, an H shape, a bow-tie shape, or any other suitable shape, such as the shapes described in, U.S. Pat. Nos. 3,738,364; 5,911,712; 6,740,070; 6,887,266; and 6,953,456. A pledget can be any suitable size prior to compression, such as from about 30 mm to about 100 mm in length and from about 30 mm to about 80 mm in width. The overall basis weight of the absorbent material can be any suitable basis weight, such from about 150 gsm to about 1,250 gsm depending upon desired absorbent capacity. The materials for a pledget and tampon can be formed into a fabric, web, or batt that is suitable for use in the absorbent material by any suitable method such as airlaying, carding, wetlaying, hydroentangling, needling or other known techniques. In certain embodiments, a pledget may be a laminar structure comprising individual distinct layers of absorbent material. In those embodiments wherein the pledget comprises a laminar structure, the discrete layers may be formed from a single absorbent material or from differing absorbent materials. Further, the layers of absorbent material may have differing densities.

A tampon can additionally include a withdrawal member. The withdrawal member can be any suitable configuration, such as one or more cords, strings, finger covers, ribbons, an extension of a material of the device, or combinations thereof. The withdrawal member can be made of any suitable material, such as cotton or rayon. The withdrawal member can optionally be provided with a secondary absorbent member, such as a mass of secondary absorbent material attached to the withdrawal cord proximate the withdrawal end of the tampon. Secondary absorbent members that may be used are described in, e.g., U.S. Pat. No. 6,258,075.

A tampon may include one or more overwraps. The overwrap can be any suitable material, such as, for example, rayon, cotton, bicomponent fibers, polyethylene, polypropylene, other suitable natural or synthetic fibers known in the art, and mixtures thereof. In certain embodiments, the tampon can comprise an overwrap material that substantially encloses the compressed tampon. In addition, or alternatively, the tampon can include an overwrap material that extends beyond the withdrawal end and forms a finger cover or absorbent skirt.

In certain embodiments, a tampon can be inserted digitally. In certain embodiments, when a tampon is intended to be digitally inserted, a finger indent may be provided at the withdrawal end of the tampon to aid in insertion, such as finger indents as described in U.S. Pat. No. 6,283,952. In certain embodiments, a tampon can be inserted using an applicator. Any suitable applicator can be used, including, for example, tube and plunger type arrangements that can be plastic, paper, or other suitable material, and compact type applicators.

The present invention is further illustrated by the following examples, which should not be construed as limiting in any way.

EXAMPLES

The examples demonstrate the reduction in microwave drying time for pledgets including metallic cation salt compared to the microwave drying time for pledgets including water only. The reduction in microwave drying time for the pledget demonstrates a corresponding reduction in microwave drying time for a tampon, which is a compressed pledget. Therefore, it is believed the reduction in microwave drying time for the tampon provides for a reduced time to stabilize the tampon. It is further believed the time to stabilize a tampon is reduced when the microwave drying time is reduced, as the reduction in moisture content (drying) of a tampon stabilizes the tampon.

Example 1

This example demonstrates the reduction in the amount of microwave drying time for a pledget including calcium chloride, in the form of a calcium chloride solution, to reach a moisture content of about 20% or less, as compared to the amount of microwave drying time for a pledget including water only to reach a moisture level of about 20% or less. However, the reduction in microwave drying time for a pledget including calcium chloride is reduced to the same extent as compared to the microwave drying time of a pledget including water only if the final moisture content, for example a final moisture content of 20%, 15%, 10%, or 5%, of the pledget including calcium chloride is the same as that of a pledget including water only.

Materials and Methods

In this example, the reduction of moisture content using microwave drying in a pledget was measured by the following procedure.

Pledgets made from cotton were used. The pledgets were measured to find the initial weight using a balance accurate to 0.01 g (such as, a Mettler PJ360). Calcium chloride solution was prepared by the addition of 1.70 g $CaCl_2$ to 1,000 ml $H_2O$, resulting in a solution with a calcium chloride concentration of 1.7 mg/ml (15.3 mM). The desired amount of calcium chloride solution, which is determined by the desired moisture content, was added to the pledget, and the pledget was weighed to find the wet weight. In this example, the amount of calcium chloride solution added was about 7 g/g of pledget. A control pledget was prepared using water only.

The pledgets were then placed in a microwave oven (Whirlpool MT415SPB: 1200 W) which was then activated. The microwave drying was stopped at specified intervals and the pledgets were weighed. Microwave drying and weighing was repeated until the pledgets had a moisture content of about 20% or less. About a 20% or less moisture content was used as an approximate measurement of a dry tampon or pledget. For the examples, about a 20% or less moisture content was believed to correlate with the moisture content of a stabilized tampon. However, it should be noted that a stabilized tampon may have a lower or greater moisture content. For example, the moisture content of a stabilized tampon may depend upon such factors as tampon density, size, volume or shape; the type of absorbent material used; or any other factors known to those of ordinary skill in the art. The following was calculated for the example: (1) initial water content of pledgets; (2) time to microwave pledgets to a moisture content of about 20% or lower; (3) reduction of time to microwave pledgets to a moisture content of about 20% or lower with calcium solution compared to control pledget lacking calcium solution; and (4) moisture content of pledgets after microwave drying.

Results

As shown in Table 1 and Table 2, the addition of calcium chloride solution to a pledget results in a reduction in microwave drying time to reach a moisture content of about 20% or less and improved microwave drying efficiency, compared to a pledget prepared with water only.

TABLE 1

Time to Reduce the Moisture Content of a Pledget Including Water to a Moisture Content of About 20% or Less

| H2O | Dry weight (g) | Wet weight (g) | Weight after drying 60 seconds | Weight after drying 120 seconds | Weight after drying 180 seconds | Weight after drying 240 seconds | Weight after drying 300 seconds | Moisture content (%) after drying 300 seconds |
|---|---|---|---|---|---|---|---|---|
| Control1 | 1.30 | 9.41 | 4.82 | 3.39 | 2.53 | 1.89 | 1.48 | 14.1 |
| Control1 | 1.27 | 9.63 | 5.66 | 3.51 | 2.55 | 1.91 | 1.45 | 14.2 |
| Control1 | 1.28 | 8.48 | 5.41 | 3.32 | 2.38 | 1.78 | 1.41 | 10.4 |
| Average | 1.28 | 9.17 | 5.30 | 3.41 | 2.49 | 1.86 | 1.45 | 12.9 |
| SD | 0.02 | 0.61 | 0.43 | 0.09 | 0.10 | 0.07 | 0.04 | 2.2 |

TABLE 2

Time to Reduce the Moisture Content of a Pledget Including 15 mM $CaCl_2$ to about 20% or Less

| 15 mM CaCl2 solution | Dry weight (g) | Wet weight (g) | Weight after drying 60 seconds | Weight after drying 90 seconds | Weight after drying 110 seconds | Moisture content (%) after drying 110 seconds |
|---|---|---|---|---|---|---|
| Test 1 | 1.26 | 9.06 | 2.52 | 1.57 | 1.30 | 3.2 |
| Test 1 | 1.25 | 8.64 | 2.14 | 1.46 | 1.29 | 3.4 |
| Test 1 | 1.22 | 9.33 | 1.97 | 1.34 | 1.28 | 4.8 |
| Average | 1.24 | 9.01 | 2.21 | 1.45 | 1.29 | 3.8 |
| SD | 0.02 | 0.35 | 0.28 | 0.12 | 0.01 | 0.9 |

As shown in Table 1, the time to microwave dry the control pledget (water only) to a moisture content of about 20% or less was measured at 300 seconds. As shown in Table 2, the time to microwave dry the test pledget ($CaCl_2$) to a moisture content of about 20% or less was measured at 110 seconds. As such, this example demonstrates that addition of calcium chloride solution to a pledget results in a reduction in microwave drying time and improved microwave drying efficiency compared with a pledget prepared with water only. The improved microwave drying efficiency is a result of the reduced use time of the source of microwave radiation, in this example a 1,200 W microwave oven, to lower the moisture content of a pledget to about 20% or less.

Example 2

This example demonstrates the reduction in the microwave drying time for a pledget including calcium chloride solution compared to the microwave drying time for a pledget including water only.

Materials and Methods

In this example, cotton and rayon pledgets were provided. The amount of time to reduce the pledgets to a moisture content of about 20% or less was measured by the procedure described in Example 1.

Results

Figure 1:
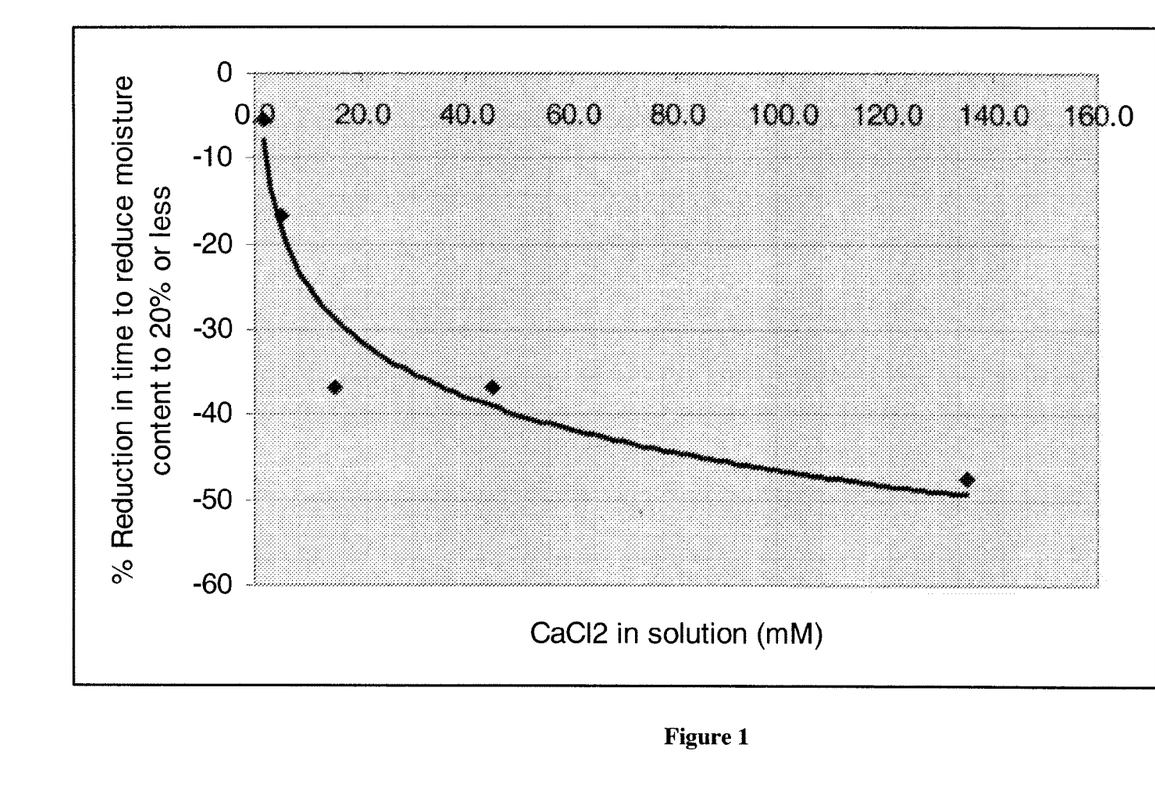
FIG. 1 is a graph showing the percent reduction in microwave drying time compared to control with increasing calcium chloride concentration.

FIG. 1 shows an increased percent reduction in the time to reduce the moisture content of a pledget to about 20% or less at increasing calcium chloride concentrations. For example, as shown in FIG. 1, addition of about 5 mM calcium chloride solution to a pledget results in about a 17% reduction in the time to reduce the moisture content of a pledget to about 20% or less, as compared to addition of water only to a pledget, while addition of about 15 mM calcium chloride results in about a 37% reduction in time, and addition of about 135 mM calcium chloride results in about a 47% reduction in time. Thus, as shown in FIG. 1, the addition of calcium chloride solution in increasing concentrations to a pledget results in increased percent reductions in the time to reduce the moisture content of a pledget to about 20% or less, as compared to a pledget including water only.

Example 3

Figure 2:
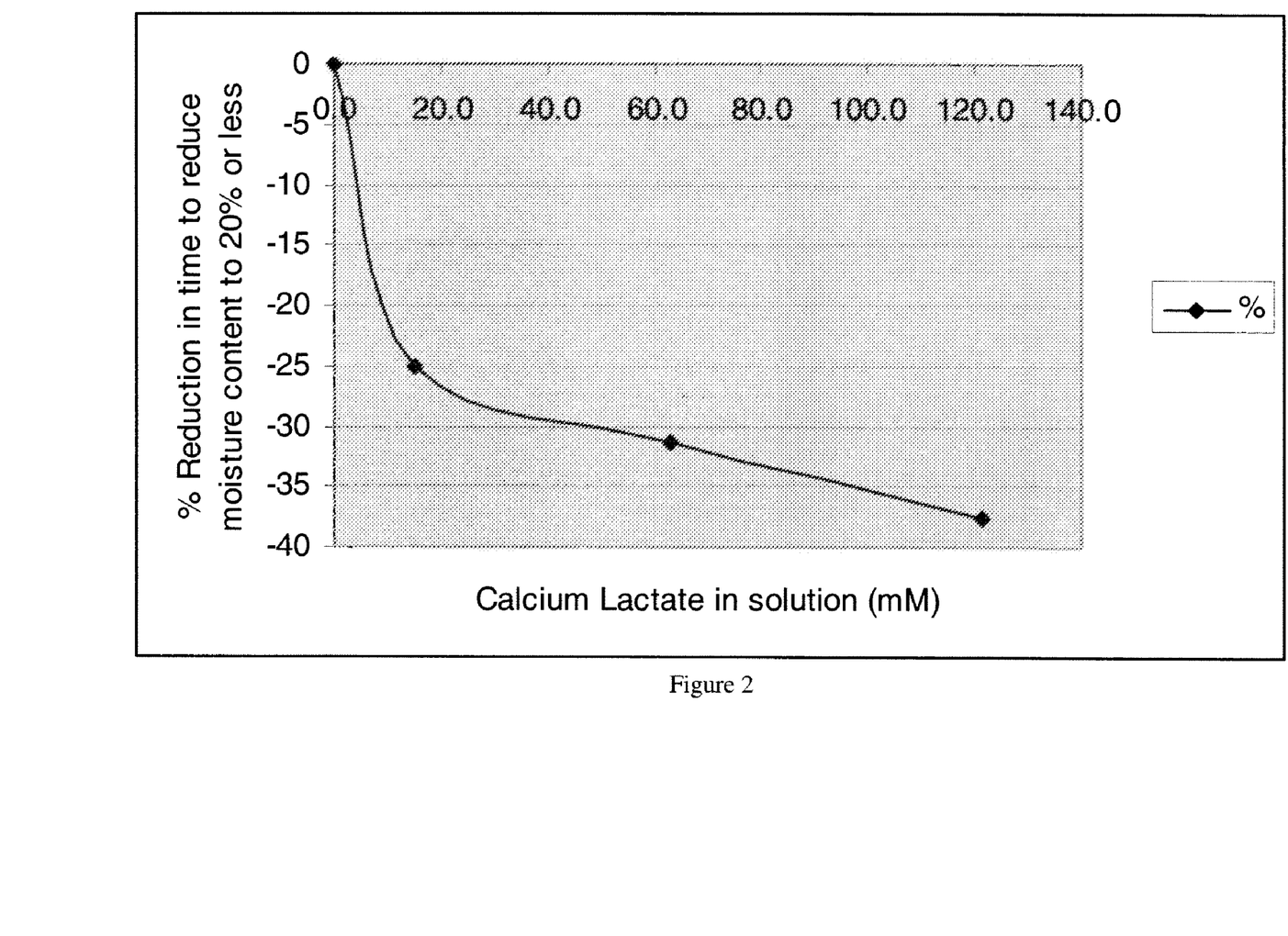
FIG. 2 is a graph showing the percent reduction in microwave drying time compared to control with increasing calcium lactate concentration.

As shown in FIG. 2, this example demonstrates the reduction in the time to reduce the moisture content of a pledget to about 20% or less using microwave radiation for a pledget including calcium lactate (organic metallic cation salt) solution, as compared to the time to reduce the moisture content of a pledget to about 20% or less using microwave radiation of a pledget including water only.

Materials and Methods

In this example, cotton and rayon pledgets were provided. The times for the pledgets to reach a moisture content of about 20% or less were measured by the procedure described in Example 1.

Results

FIG. 2 shows an increased percent reduction in the time to reduce a pledget's moisture content to about 20% or less at increasing calcium lactate concentrations. For example, as shown in FIG. 2, addition of about 15.2 mM calcium lactate solution to a pledget results in about a 25% reduction in time compared to a pledget including water only, while addition of about 63.1 mM calcium lactate results in about a 31% reduction in time, and addition of about 121.3 mM calcium lactate results in about a 38% reduction in time. Thus, as shown in FIG. 2, the addition of calcium lactate solution in increasing concentrations to a pledget results in increased percent reductions in the time to reduce the moisture content of a pledget to about 20% or less using microwave radiation, as compared to a pledget including water only.

Example 4

This example demonstrates the reduction in time to reach a moisture content of about 20% or less using microwave radiation for pledgets including different metallic cation salts, as compared to a pledget including water only.

Materials and Methods

In this example, cotton and rayon pledgets were provided. The times to reduce the moisture content of the pledgets to about 20% or less using microwave radiation were measured by the procedure described in Example 1.

Results

The effect of adding various metallic cation salt solutions to pledgets on the reduction of the time to reach a moisture content of about 20% or less using microwave radiation is shown in Table 4.

TABLE 4

Reduction in the Time of Pledgets Including Various Organic and Inorganic Metallic Cation Salt Solutions to Reach A Moisture Content of about 20% or Less

| Metallic cation salt | Concentration (mM) | Reduction in Drying Time | % moisture in fiber |
|---|---|---|---|
| Calcium Lactate | 15.2 | −25% | 14.5 |
| Sodium Chloride | 15.4 | −29% | 9.8 |
| Magnesium Chloride | 15.8 | −42% | 14.9 |
| Calcium Chloride | 15.0 | −37% | 9.2 |

Figure 3:
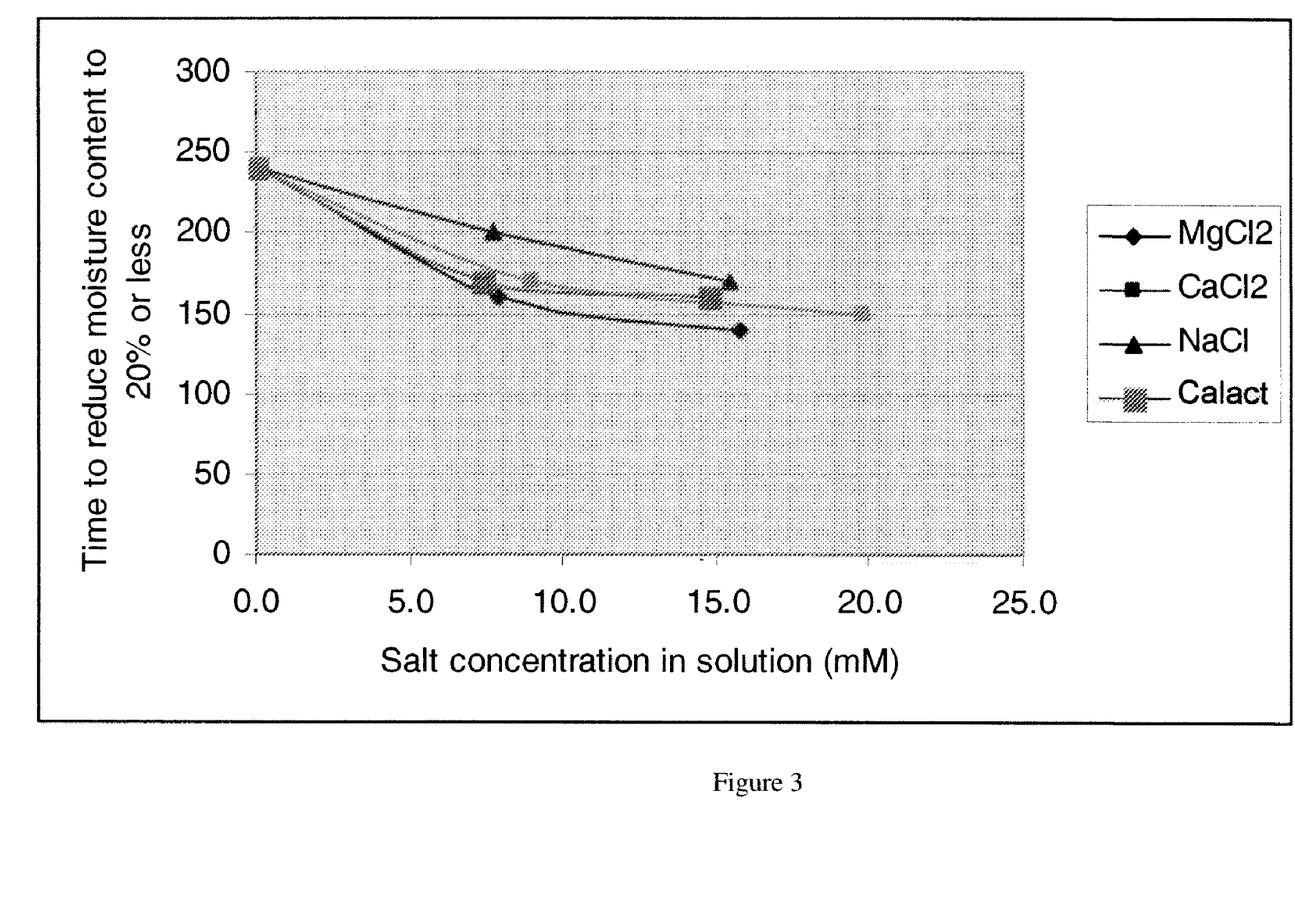
FIG. 3 is a graph showing the microwave drying time in seconds with increasing metallic cation salt concentration at 1,200 W of microwave power.
Figure 4:
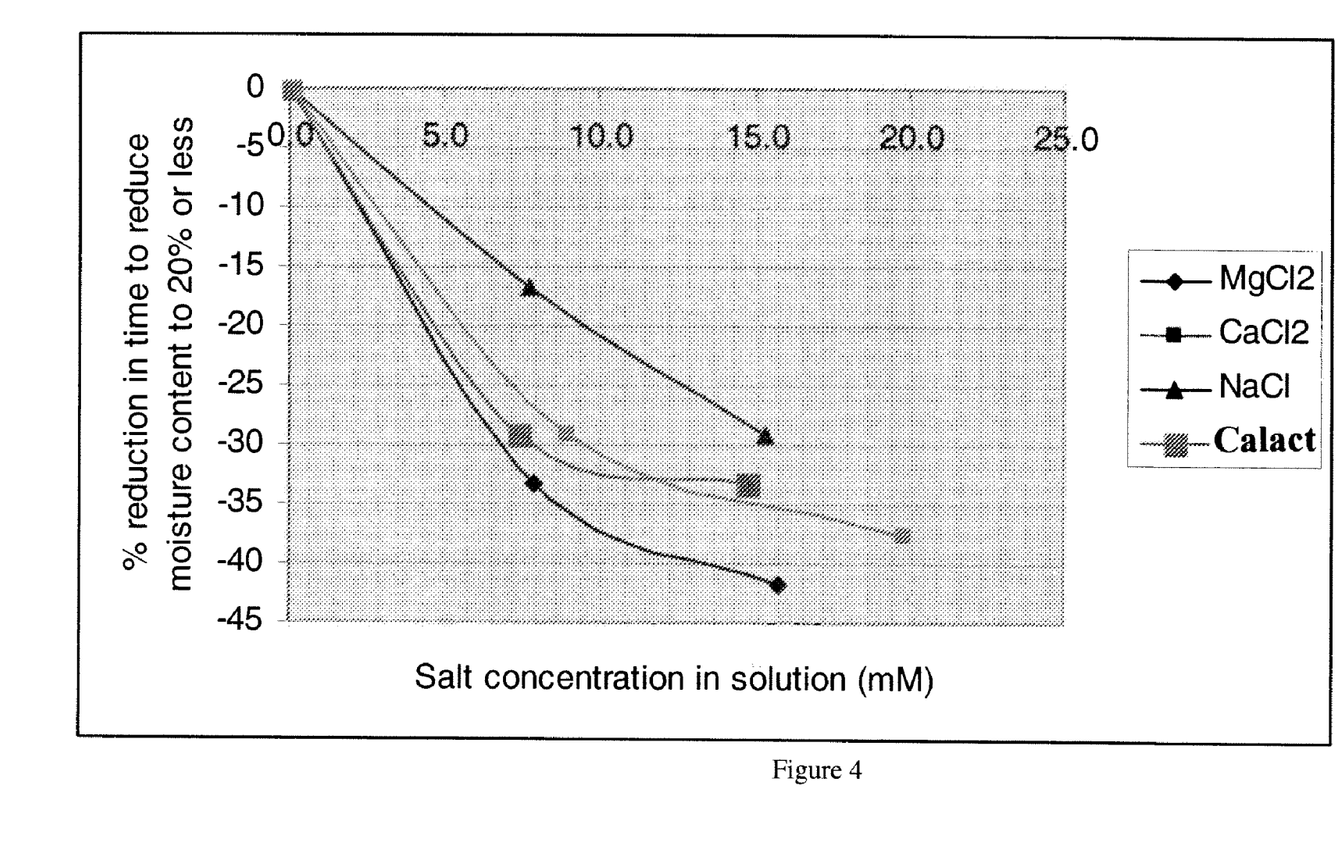
FIG. 4 is a graph showing the percent reduction in microwave drying time compared to control with increasing metallic cation salt concentration.

As shown in Table 4, the addition of calcium lactate, sodium chloride, magnesium chloride, and calcium chloride, solutions to pledgets results in a reduction in the time to reach a moisture content of about 20% or less using microwave radiation and improved microwave drying efficiency compared with a pledget including water only. The time to reach a moisture content of about 20% or less in seconds for calcium chloride, magnesium chloride, sodium chloride, and calcium lactate is shown in FIG. 3. The reduction in the time to reach a moisture content of about 20% or less compared to the control is shown in FIG. 4. As such, this example demonstrates that addition of various metallic cation salt solutions to a pledget results in a reduction in the time to reach a moisture content of about 20% or less using microwave radiation and improved microwave drying efficiency compared with a pledget prepared with water only.

Example 5

Figure 5:
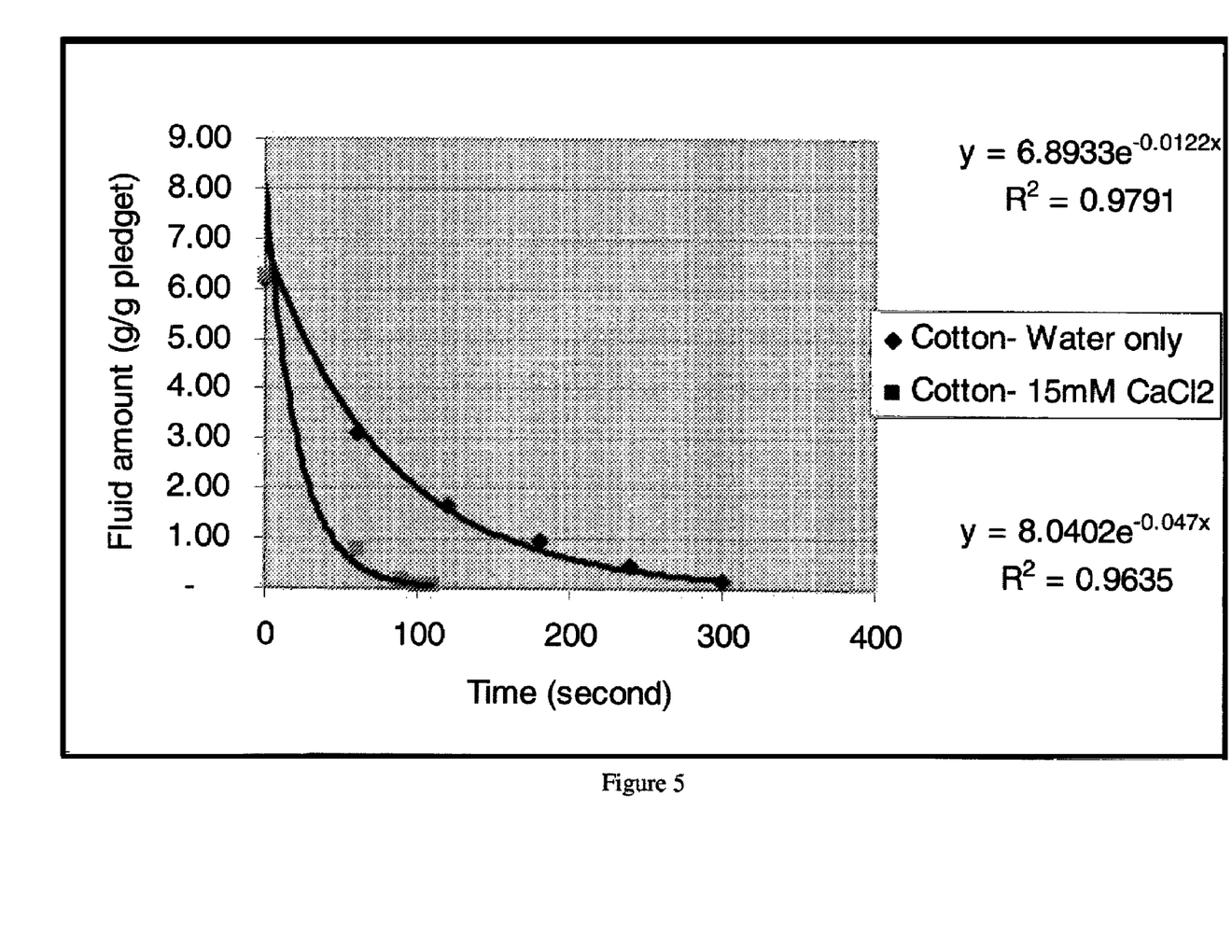
FIG. 5 is a graph showing the reduction in fluid amount over time with addition of calcium chloride compared to control.
Figure 6:
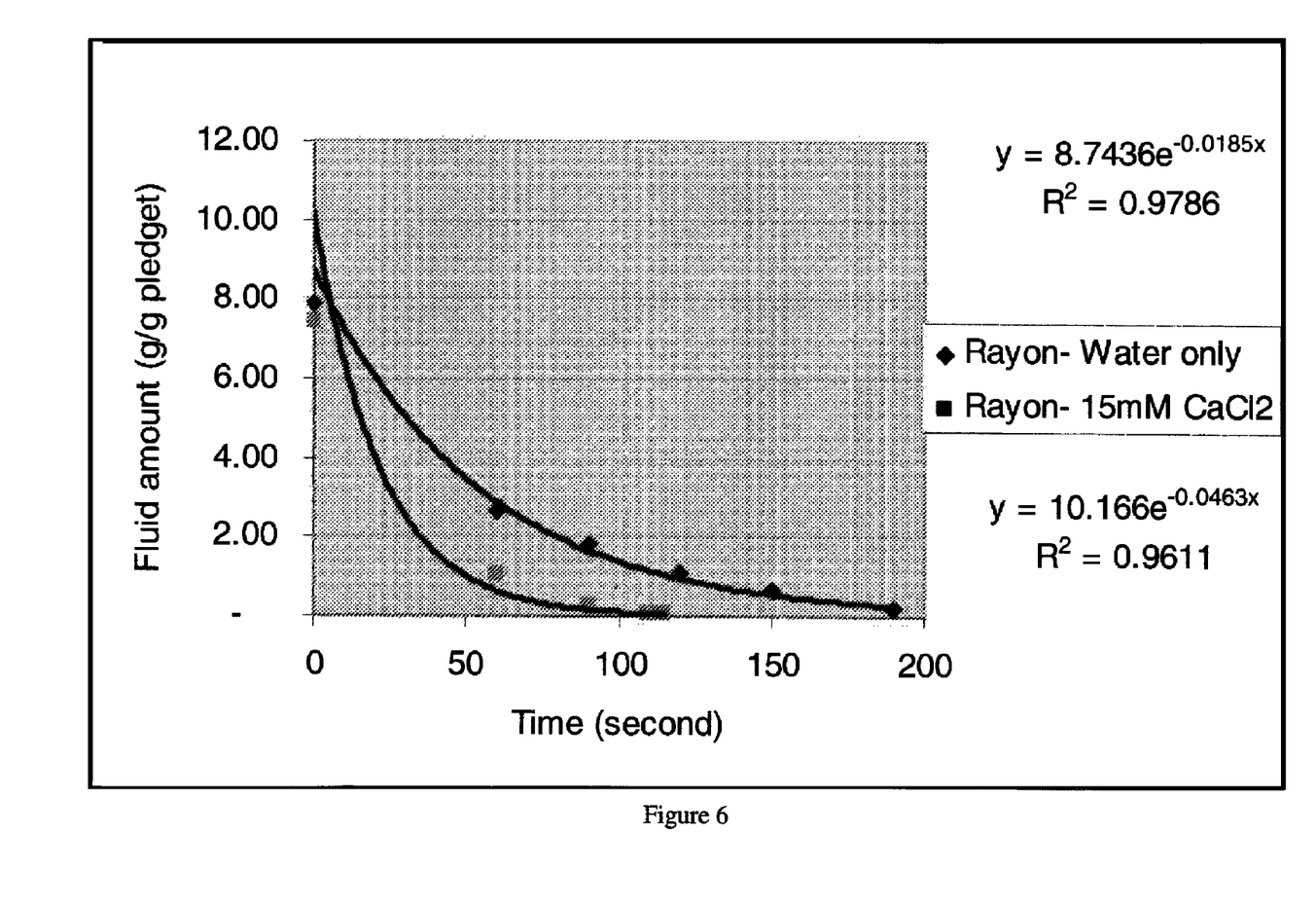
FIG. 6 is a graph showing the reduction in fluid amount over time with addition of calcium chloride compared to control.
Figure 7:
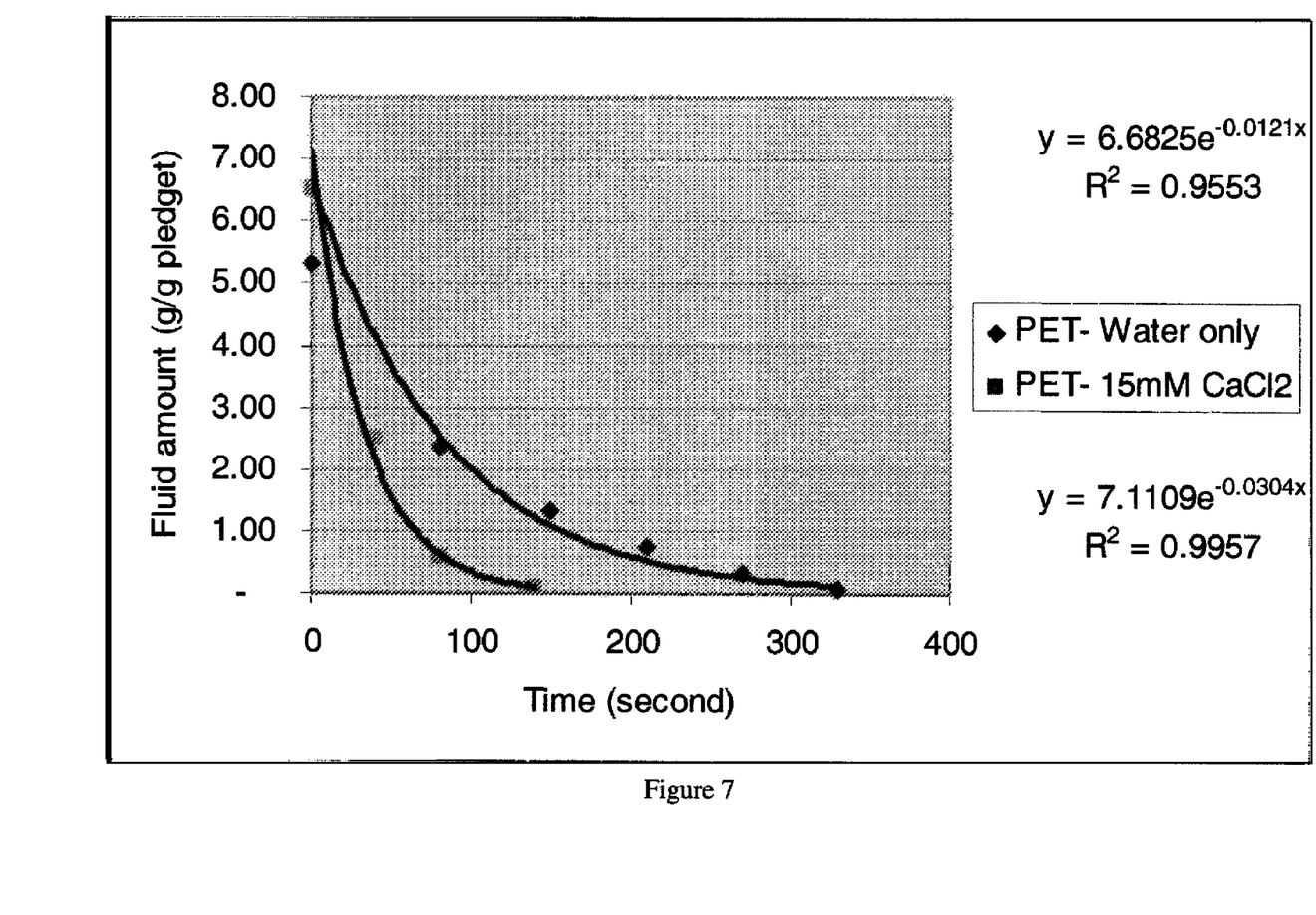
FIG. 7 is a graph showing the reduction in fluid amount over time with addition of calcium chloride compared to control.

As shown in FIG. 5-7, this example demonstrates that the amount of fluid in the pledget decreases exponentially with microwave drying.

Materials and Methods

Cotton, rayon, and polyester (PET) pledgets were provided. The time to remove about 50% of the fluid (half-life) was calculated to describe the drying behavior of a pledget. In this example, the times to remove about 50% of the fluid of the pledget were measured by the procedure described in Example 1. 15 mM calcium chloride solution was added to each pledget type.

Results

The reduction in fluid amount over time is shown in FIGS. 5-7. As shown in FIG. 5, the time to reduce the moisture content to 50% for cotton pledgets with added calcium chloride solution was about 3.8 times faster than cotton pledgets with water only. As shown in FIG. 6, the time to reduce the moisture content to 50% for rayon pledgets with added calcium chloride solution was about 2.5 times faster than rayon pledgets with water only. In addition, as shown in FIG. 7, the time to reduce the moisture content to 50% for PET pledgets with added calcium chloride solution was about 2.5 times faster than PET pledgets with water only.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for stabilizing a tampon, the method comprising the steps of:
    (a) providing a pledget having a moisture content and comprising one or more metallic cation salts;
    (b) compressing the pledget to produce a tampon having a moisture content and comprising one or more metallic cation salts;
    (c) applying microwave radiation to the tampon for a time sufficient to stabilize the tampon; and
    wherein the stabilization time is reduced compared to the stabilization time for a tampon having a moisture content, but lacking one or more metallic cation salts.

2. The method of claim 1, wherein the one or more metallic cation salts is an inorganic metallic cation salt, organic metallic cation salt, or combinations thereof.

3. The method of claim 1, wherein the one or more metallic cation salts is at least one of a calcium salt, a ferric salt, a magnesium salt, a sodium salt, a strontium salt, a barium salt, an aluminum salt, a copper salt, a zinc salt, potassium salt, or combinations thereof.

4. The method of claim 3, wherein the one or more metallic cation salts is calcium chloride, calcium lactate, calcium citrate malate, or combinations thereof.

5. The method of claim 1, wherein the stabilization time is reduced by at least about 20%.

6. The method of claim 1, wherein the stabilization time is reduced by at least about 30%.

7. The method of claim 1, wherein the stabilization time is reduced by at least about 40%.

8. The method of claim 1, wherein the one or more metallic cation salts is added in a concentration of at least about 2.5 mM.

9. The method of claim 1, wherein the tampon has a moisture content greater than about 20% prior to step (c).

10. The method of claim 1, wherein the tampon has a moisture content of less than about 20% after step (c).

11. The method of claim 1, wherein the tampon comprises at least one of cotton, rayon, polyester, or combinations thereof.

12. A method for stabilizing a tampon, the method comprising the steps of:
    (a) providing a pledget comprising one or more metallic cation salts;
    (b) compressing the pledget to produce a tampon comprising one or more metallic cation salts;
    (c) providing the tampon with a moisture content;
    (d) applying microwave radiation to the tampon for a time sufficient to stabilize the tampon; and
    wherein the stabilization time is reduced compared to the stabilization time for a tampon having a moisture content, but lacking one or more metallic cation salts.

13. The method of claim 12, wherein the tampon is provided with a moisture content during compression, following compression, or both.

14. The method of claim 12, wherein the one or more metallic cation salts is an inorganic metallic cation salt, organic metallic cation salt, or combinations thereof.

15. The method of claim 12, wherein the one or more metallic cation salts is at least one of a calcium salt, a ferric salt, a magnesium salt, a sodium salt, a strontium salt, a barium salt, an aluminum salt, a copper salt, a zinc salt, a potassium salt, or combinations thereof.

16. The method of claim 12, wherein the one or more metallic cation salts is calcium chloride, calcium lactate, calcium citrate malate, or combinations thereof.

17. The method of claim 12, wherein the one or more metallic cation salts is added in a concentration of at least about 2.5 mM.

18. The method of claim 12, wherein the tampon comprises at least one of cotton, rayon, polyester, or combinations thereof.

19. A method for stabilizing a tampon, the method comprising the steps of:
    (a) providing a pledget;
    (b) compressing the pledget to produce a tampon;
    (c) providing the tampon with a moisture content and one or more metallic cation salts;
    (d) applying microwave radiation to the tampon for a time sufficient to stabilize the tampon; and
    wherein the stabilization time is reduced compared to the stabilization time for a tampon having a moisture content, but lacking one or more metallic cation salts.

20. The method of claim 19, wherein the tampon is provided with a moisture content and one or more metallic cation salts during compression, following compression, or both.

* * * * *